US00PP08615P

United States Patent [19]

Evers

[11] Patent Number: Plant 8,615

[45] Date of Patent: Mar. 1, 1994

[54] HYBRID TEA ROSE PLANT NAMED 'TANEKIAM'

[75] Inventor: Hans Evers, Uetersen, Fed. Rep. of Germany

[73] Assignee: Bear Creek Gardens, Inc., Medford, Oreg.

[21] Appl. No.: 986,434

[22] Filed: Dec. 4, 1992

[51] Int. Cl.[5] ..... A01H 5/00

[52] U.S. Cl. ..... Plt./11

[58] Field of Search ..... Plt. 18, 11, 14

*Primary Examiner*—Howard J. Locker
*Assistant Examiner*—Elizabeth C. Kemmerer
*Attorney, Agent, or Firm*—Klarquist, Sparkman, Campbell, Leigh and Whinston

[57] ABSTRACT

Hybrid Tea rose capable of high production of white blooms with elegant bud flower shape on strong, wiry stems having long vase life.

1 Drawing Sheet

The present invention relates to a new and distinct variety of rose plant of the Hybrid Tea class which was originated by me by crossing two unnamed seedlings.

The primary objective of this breeding was to produce a new rose variety having light pastel pink blooms, high production and a long vase life. The objective was substantially achieved along with other desirable improvements as evidenced by the following unique combination of characteristics which are outstanding in the new variety and which distinguish it from its parents, as well as from all other varieties of which I am aware:

1. High production in greenhouse (180–200 stems per $m^2$) of long stemmed roses;
2. Few thorns;
3. Well shaped long lasting cut flower;
4. Strong, wiry stems.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—*Rosa hybrida.*

*Commercial.*—Hybrid Tea.

FLOWER

Observations made from specimens grown in a greenhouse environment in Somis, Calif., from January through June, 1992.

Blooming habit: Recurrent.

Bud:

*Size.*—2" when the petals start to unfurl.

*Form.*—Very long, pointed ovoid.

*Color.*—When sepals first divide, bud color is Yellow-White Group 158C with the tip of the flower being Red Group 49A. When half blown, the upper sides of the petals are White Group 155B with the center of the flower showing an overtone of Red Group 49A; and the lower sides of the petals are White Group 155B.

*Sepals.*—Color: Green Group 138A. Surface texture: Covered with fine hairs. There are three lightly appendaged sepals. There are two unappendaged sepals with hairy edges.

*Receptacle.*—Color: Green Group 137A. Shape: Funnel. Size: Broad, long (⅜" long×5/16" wide). Surface: Smooth.

*Peduncle.*—Length: Long, 3½". Surface: Glandular. Color: Medium green. Strength: Stiff, erect.

Bloom:

Size.—Large. Average open size is 4½–5".

*Borne.*—Singly.

*Stems.*—Long, strong, wiry, 22–28".

*Form.*—When first open: High centered. Permanence: Retains its form to the end, outer petals curl back.

*Petalage.*—Number of petals under normal conditions: 30.

*Color.*—The upper side of the petals is White Group 155B with some pink on the petal edge (Red Group 49A). The reverse side of the petals is White Group 155B with some pink on the petal edge (Red Group 49A). The bases of the petals have a distinctive yellow coloration at the point of attachment, about ¼"×¼", with some bleeding into the bottom quarter of the petal. The major color on the upper side is White Group 155B.

*Variegations.*—None.

*Discoloration.*—The general tonality at the end of the first day: No change. At the end of the third day. Gradual fading of the pink as the flower opens becoming completely white when fully opened.

*Fragrance.*—Slight.

Petals:

*Texture.*—Thick.

*Shape.*—Round.

*Form.*—Tips slightly recurved, edges slightly quilled.

*Arrangement.*—Imbricated, with few petaloids in the center.

*Persistence.*—Drops off cleanly.

*Lastingness.*—On the plant: Long, 6–7 days. As a cut flower: Very long, 10–12 days.

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Red.

*Stigmas.*—Color: Greenish white.

Form: Bush.

Growth: Very vigorous upright and branching.

Foliage:

*Number of leaflets on normal mid-stem leaves.*—5 or 7 Upright, branching.

*Size.*—Large, 6"×4".

*Quantity.*—Normal.

*Color.*—New foliage: Reddish. Old foliage: Dark green.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Rough with prickles.

*Stipules.*—Medium, edged with glands.

*Disease resistance.*—Susceptible to mildew under normal growing conditions in a greenhouse at Somis, Calif.

Wood:

*New wood.*—Color: Reddish. Bark: Smooth.

*Old wood.*—Color: Green. Bark: Smooth.

Prickles:

*Quantity.*—On main canes from base: Few. On laterals from main canes: Few.

*Form.*—Medium, straight.

*Color when young.*—Red.

Small prickles:

*Quantity.*—On main stalks: None. On laterals: None.

I claim:

1. A new and distinct variety of rose plant of the Hybrid Tea class, substantially as herein shown and described, characterized particularly as to novelty by the unique combination of its high production of long stemmed cut flowers, its elegant bud and flower shape, its good vase life, its few thorns and its strong wiry stems.

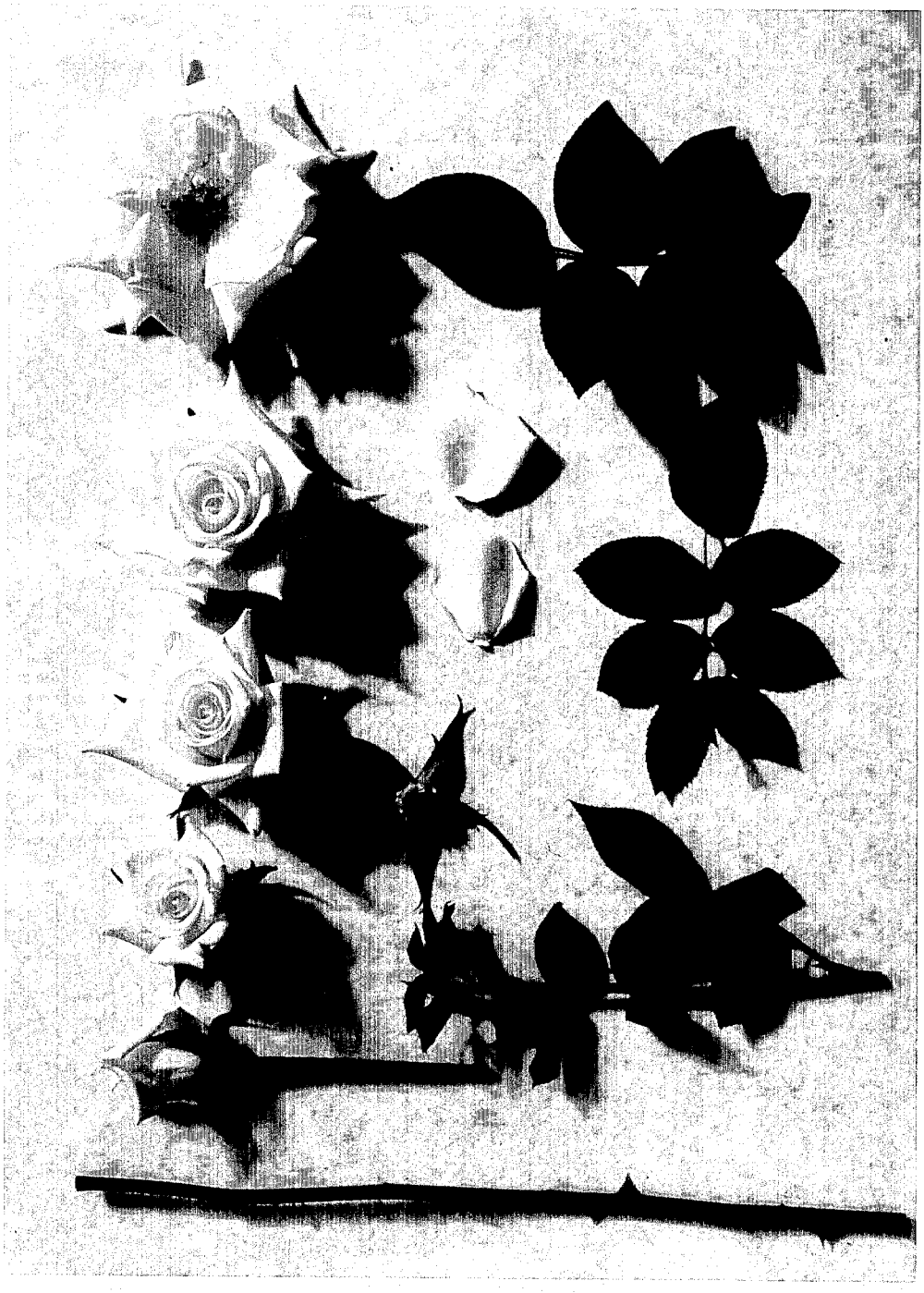

* * * * *